United States Patent [19]

Chambron

[11] Patent Number: 4,484,121
[45] Date of Patent: Nov. 20, 1984

[54] SERVOCONTROL BY ULTRASONICS OF THE RELATIVE POSITION OF TWO MECHANICAL COMPONENTS

[75] Inventor: Edmond Chambron, Paris, France
[73] Assignee: Thomson-CSF, Paris, France
[21] Appl. No.: 387,143
[22] Filed: Jun. 10, 1982
[30] Foreign Application Priority Data
Jun. 12, 1981 [FR] France ................ 81 11610
[51] Int. Cl.³ .............................................. G05B 1/06
[52] U.S. Cl. .................................... 318/640; 318/675; 356/5; 250/491.1
[58] Field of Search ............... 318/640, 675, 685, 480; 356/5; 250/491.1

[56] References Cited
U.S. PATENT DOCUMENTS
3,775,582 11/1973 Iceland .................. 318/640 X
4,095,160 6/1978 Sedlmayer et al. ............ 318/675
4,204,146 5/1980 Peiffert et al. .................. 318/640
4,292,576 9/1981 Watts ............................ 318/640

FOREIGN PATENT DOCUMENTS
0032479 3/1977 Japan ..................... 318/640

Primary Examiner—B. Dobeck
Attorney, Agent, or Firm—Cushman, Darby & Cushman

[57] ABSTRACT

A servocontrol permits the alignment of a slave mechanical component with a master mechanical component. A probe measures its distance from the master component and another probe measures it distance from the slave component. A circuit processes a square wave pulse whose duration is proportional to the distance separating the master component from the slave component. A motor is supplied with power until the pulse ends.

7 Claims, 4 Drawing Figures

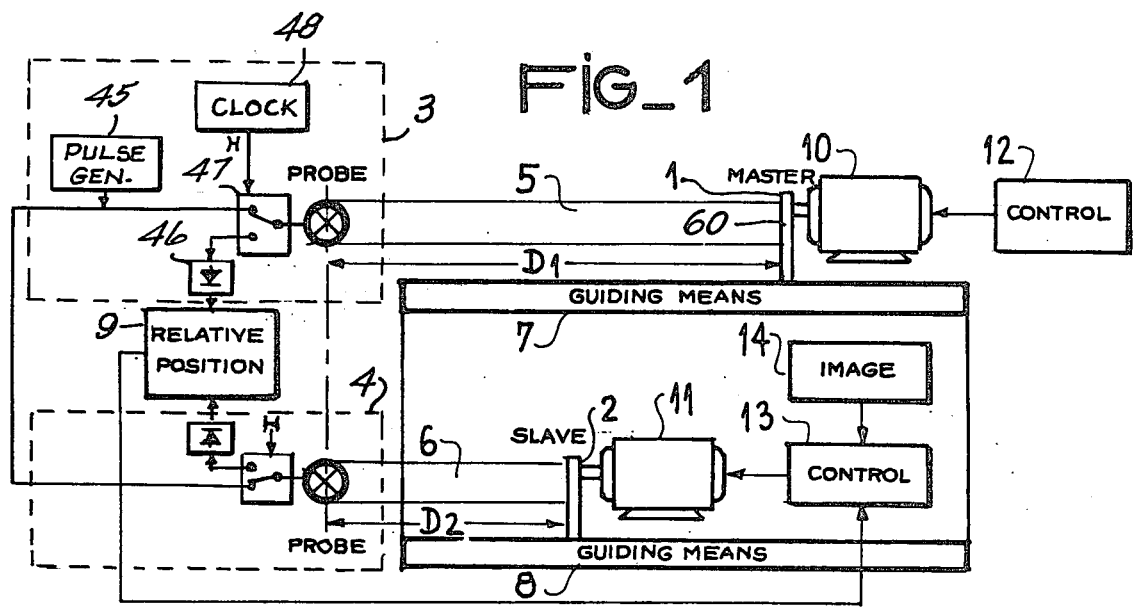
FIG_1
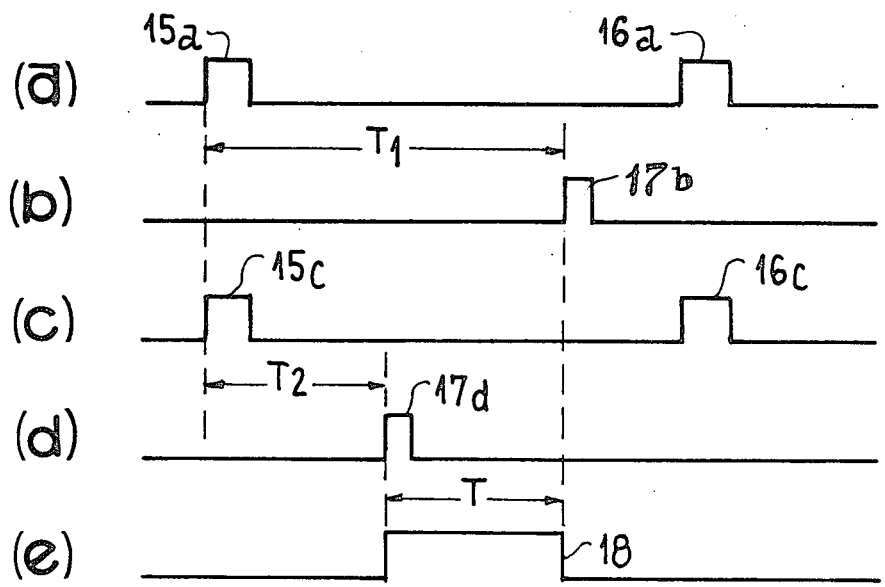
FIG_2

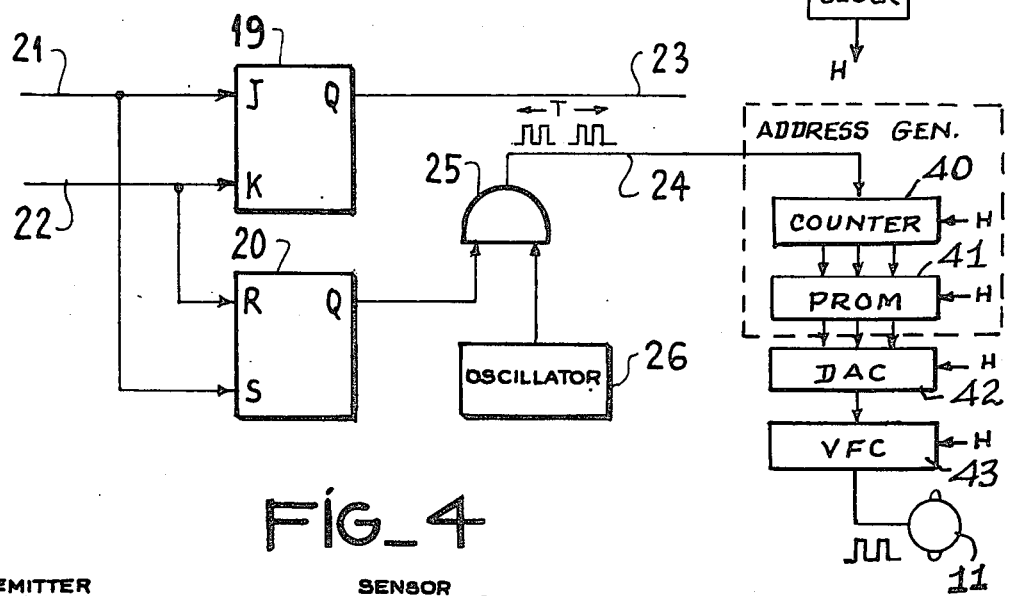
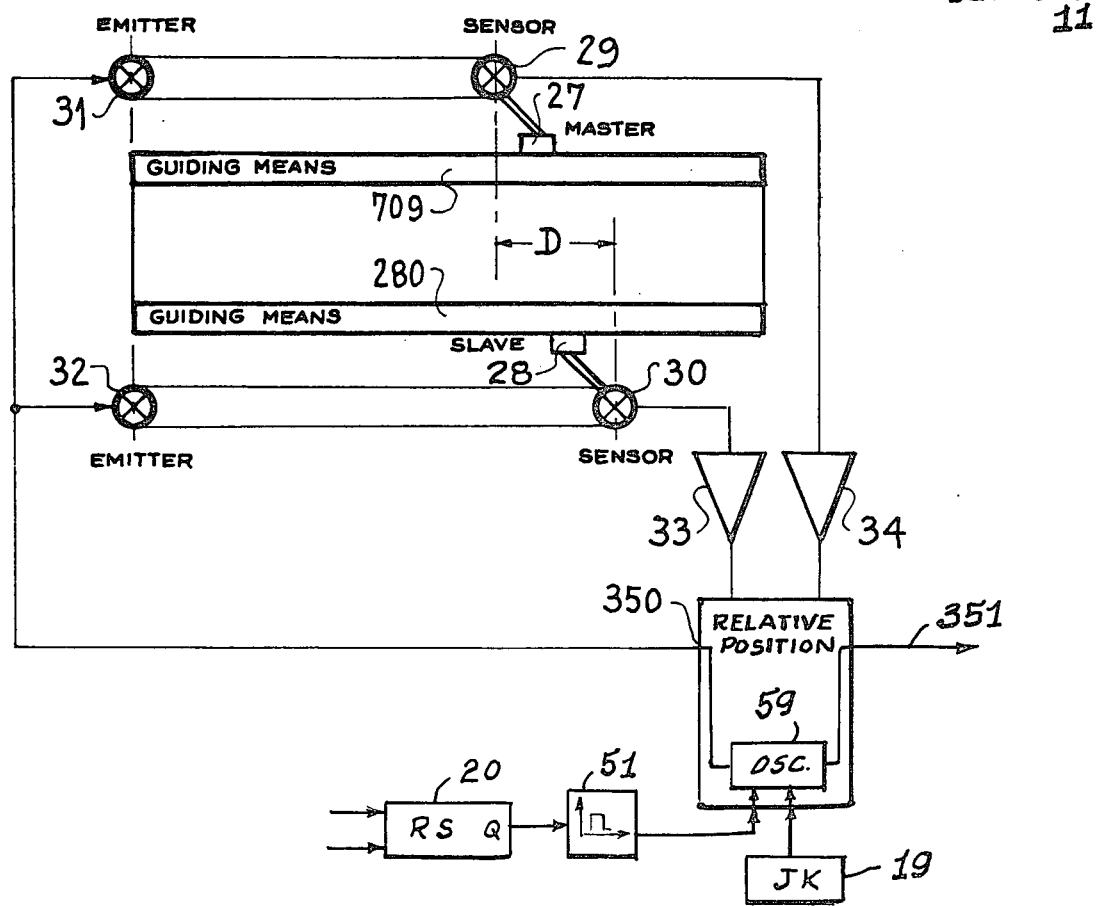

SERVOCONTROL BY ULTRASONICS OF THE RELATIVE POSITION OF TWO MECHANICAL COMPONENTS

BACKGROUND OF THE INVENTION

The present invention relates to a servocontrol by ultrasonics of mechanical components in the relative master - slave position and radiology apparatus incorporating such a servocontrol. It is in particular used in radiology, where an operator brings a radiation source into a position at where it is a needed to align a detector of the X-ray image with the source.

The present invention is used in the servocontrol of the relative positions.

In the prior art, it is known to use ultrasonics for controlling displacements of mechanical components, which carry transducers and receive remote control commands by ultrasonics. The acquisition of data of the distance of the mechanical component dependent on a point of origin is brought about by echo reflection measurement. An echo transmitted by a transmitting probe is reflected onto the mechanical component and returns after a certain time, whose measurement indicates the absolute position found of the mechanical component. To obtain a satisfactory accuracy, such devices require a large amount of electronics. It is an advantage of the present invention that it considerably simplifies the control electronics and improves the relative precision of these servocontrols.

Distance measuring solutions using ultrasonic beams through the air have particularly been developed for the setting of focal lengths of photographic lenses. The remote control of household or domestic appliances such as television sets by ultrasonics through the air is well known. The application of such methods to metric servocontrol with an accuracy of better than 1 mm involves signal coding on several tens of bits, which considerably increases the weight and cost of the electronics. It is an advantage of the present invention that it makes it possible to considerably reduce the number of bits to be processed for high precision levels, even in the case of displacements of several meters.

The invention is particularly advantageous in that it can be adapted to solve various problems. More particularly, in radiology it is known that the alignment of two movable mechanical components is a difficult problem. This is the case with an X-ray source, which has to be accurately positioned on the reception optics of an X-ray film holder.

The present invention permits an alignment of these two components with a high degree of accuracy and without increasing the size of the electronic means.

BRIEF SUMMARY OF THE INVENTION

The present invention therefore relates to a servocontrol by electronics of mechanical components in relative positions, each of the mechanical components between moved by motor means on guidance means, the respective positions of the different components being measured by ultrasonic probes, wherein the servocontrol also comprises means for positioning the master mechanical components, circuits for measuring the relative positions of slave mechanical components with respect to the master mechanical components with which they are associated, control circuits for the motor means of the slave mechanical components and means for positioning the slave mechanical components on positions imaging the positions of the master mechanical components.

BRIEF DESCRIPTION OF THE DRAWINGS

The invention is described in greater detail hereinafter relative to non-limitative embodiments and the attached drawings, wherein show:

FIG. 1 a diagram of a servocontrol for the relative positions according to the invention.

FIG. 2 operating diagrams of the servocontrol of FIG. 1.

FIG. 3 an embodiment of the circuit for the servocontrol according to FIG. 1.

FIG. 4 a diagram of a variant of the servocontrol according to the invention.

DETAILED DESCRIPTION OF THE PREFERRED EMBODIMENTS

FIG. 1 shows a servocontrol of the relative positions according to the invention. In such a device, the master and slave components are mechanical components movable on guidance means. They are diagrammatically represented by a master component 1 moving on guidance means 7 and a slave component 2 moving on guidance means 8. For ease of understanding purposes, the guidance means are assumed to be rectilinear and parallel. Moreover, each point of one of the guidance means 7, 8 can be considered as the orthogonal projection of one point of the facing guidance means. Thus, in the said drawing each point of one of the guidance means representing a position of the mechanical component being moved permits a corresponding image by orthogonal projection onto the facing guidance means. Ultrasonics probes 3, 4 are fixed to guidance means 7, 8. Probe 3 is associated with the master mechanical component 1 and transmits and receives an ultrasonic beam 5, which is reflected onto a reflector means 60 carried by the master component. This reflector means can be constituted by one face of the mechanical component. It can also be constituted by an auxillary device connected to the corresponding mechanical component. For a good operation of the device, it is necessary that the surface of each reflector is substantially normal to the incidence direction of the ultrasonic beam 5. The reflecting ultrasonic beam must intercept the transmitting probe. Probe 4 is associated with the slave mechanical component 2. To simplify the diagram, the position of probe 4 is the image by orthogonal projection of the position of probe 3. FIG. 1 diagrammatically shows a relative positioning of master component 1 and slave component 2 with master component at a distance D1 from probe 3 and slave component 2 at a distance D2 from probe 4. In the prior art devices, the servocontrol of the positions of each of the components is determined by the knowledge of distances D1 and D2. In the case of distances exceeding 1 metre, the number of coding bits for processing the data is very high and consequently considerably increases the weight and cost of the electronics used. In order to reduce the electronics, the present invention proposes measuring the relative distance between the slave component and the master component.

Probes 3 and 4 can be of the transmission - reception type. Such a probe comprises a pulse generator 45 and a detection circuit 46. It also comprises an electronic switch 47, which periodically switches the probe to the pulse generator and then to the detection circuit. The switch 47 is driven by a clock 48.

In FIG. 2 diagram a illustrates such an operation. Square wave pulse 15a indicates that the electronic switch of the probe has been placed in the transmission position. During this pulse, the pulse generator 45 transmits on the probe an electronic pulse train which excites, for example, a piezoelectric crystal. The crystal 49 transmits an ultrasonic wave, which can have a plurality of frequencies of approximately 40 to 60 kilohertz for a good propagation in air. After the square wave pulse 15a, the probe is switched into the reception position. In FIG. 2, the reception of an echo on such a probe is designated in diagram b by a square wave pulse 17b. A time t1 has elapsed between the transmission 15a of ultrasonic waves and reception 17b of the echo reflected by the reflectors of the associated mechanical component. Once transmitted, the ultrasonic wave traverses during time t1 a distance separating the probe from the reflector, i.e. D1 and then the return from the reflector to the probe. Thus, the distance traversed by the wave front is twice the distance separating the probe from the associated component. Therefore, time t1 is a measure of the distance D1. The reception circuit of each probe 3,4 is connected to a circuit 9 for measuring the relative positions. The master component 1 is driven by a motor 10, whose operation is controlled by a position control circuit 12, which can be manipulated by the operator, who brings the master component to the desired operating point. The slave mechanical component 2 is displaced by a motor 11 supplied by a control circuit 13 which receives image position data supplied on the one hand by an image position circuit 14 and on the other by a relative position measuring circuit 9.

The image position circuit 14 comprises an input member for the image of the position of master component 1. This member can comprise a keyboard of functions requested by the user. In particular, the user may use orthogonal projection image points. However, he may also have other transformations such as rotations, orthogonal affinities and homothetic transformations. In particular, it is possible to define a composite image consisting e.g. of an orthogonal projection of the position of the master components onto the slave component guidance rail 8, followed by a translation by a given quantity on said rail defining a particular image position of the position of the master component. This image position is the position taken into account by the servocontrol according to the invention and the final position of the slave component.

The operation of the servocontrol of FIG. 1 will now be described with the aid of FIG. 2. Diagram a represents the sequence of pulse trains transmited by probe 3, whilst diagram c represents a synchronous sequence of pulses transmitted by probe 4. In the case of FIG. 1, the ultrasonic wave transmitted by probe 4 is then reflected and creates on diagram d an echo 17d. The master mechanical component 1 is represented at a greater distance from its associated probe, so that echo 17b of the transmitted ultrasonic wave train 15a is received at a later time. Echoes 17b and 17d are supplied in the form of electrical signals by detection circuits of probes 3 and 4 to the relative position measuring circuit g, which processes a square wave pulse 18 of diagram e, whose rising front is triggered by the appearance of the first echo 17d and whose falling front is produced by the appearance of echo 17b which is the second echo received. The duration T of this square wave pulse corresponds to the reception time difference t1-t2 between echoes 17b and 17d. Thus, time T is a measure of the relative position D1-D2 of the slave component 2 with respect to the master component 1. At the end of the sequence, a new train of pulses 16a, 16c can be transmitted. The time separating two successive pulses 15a, 16a must correspond to the maximum distance between probe 3 and the controlled component. The relative position measuring circuit 9 supplies to control circuit 13 on the one hand the operation order for motor 11 and on the other the displacement direction of the slave component 2.

At a limit value D supplied by the image position circuit 14, the control circuit 14 of motor 11 of slave component 2 gives the order to said circuit 13 to stop the power supply to the motor. This leads to the servocontrol of the position of the slave component 2 to the image position supplied by the master component 1. If it is wished to obtain an alignment of the slave mechanical component 2 with the orthogonal projection image of the position of the master component 1, it is merely necessary in the case of FIG. 1 for time T to be made as small as possible. In this case, control circuit 13 supplies motor 11 until the reception time t2 of reception echo 17d is equal to time t1 of echo 17b.

FIG. 3 shows a special embodiment of the relative position measuring circuit 9. Each of the echo signals 21, 22 is simultaneously supplied to the inputs of the two circuits 19, 20. Circuit 19 detects the displacement direction to be applied to slave component 2. Thus, in the case of linear displacements, this displacement direction must reduce the distance separating the master component from the slave component. In one embodiment, such a circuit can be constituted by a flip-flop JK. Each of the rotation directions is then coded by a 1 or a 0, according to the constructionally defined code. Circuit 20 measures the time interval separating the appearance of the two echo signals. Such a circuit can comprise a flip-flop of the RS type, which changes state on each transition on one or other of its inputs. Its output processes a square wave pulse of logic voltages identical to the square wave pulse 18 of diagram e of FIG. 2. In a particular embodiment where it is necessary to bring this voltage square wave pulse 18 into the form of a binary number, it is proposed to transmit the output of flip-flop 20 to an AND gate 25, so as to validate the output of a high frequency oscillator 26. When the square wave pulse 18 rises, a pulse train is supplied to output 24 of AND gate 25. When the square wave pulse falls, the gate is blocked and the output voltage drops again to low level. The time interval T representing the duration of square wave pulse 18 can be measured by a counter.

According to a special embodiment, oscillator 26 can be connected to probes 3 and 4 via a single electronic transmission - reception switch. Only the detection circuits are provided individually for each of the probes. This ensures that square wave pulses 15a and 15c of FIG. 2 are indeed synchronous during time. In this case pulse generator 45 is replaced by the oscillator 26.

According to a special embodiment, motor 11 is a stepping motor. In such a motor, it is necessary to supply preprogrammed voltage gradients, so as to bring the motor into a particular position. A control circuit will then have an address generator 44, whose input corresponds to the output 24 of AND gate 25 of the relative position measuring circuit 9. The output of the counter 40 is the binary translation of the number of pulses supplied by the oscillator 26 during time T of square wave pulse 18. This output is connected to the address input bus of a PROM memory. Each address of this memory 49 comprises the instantaneous value of the voltage during the incrementation of the counter. Thus, the counter has as the address a number varying from 1 to N, if square wave pulse 18 makes it possible to supply N oscillations.

As the period of an oscillation is the image of a servocontrol distance step, it is possible to enter into the PROM memory a rotation speed curve of motor 11 as a function of the relative distance from the slave component to the image position of the master component in such a way that e.g. motor 11 can bring the slave component into its dependent position with a zero speed. The feedback loop is then necessarily open, Which ensures a good stability of the system.

In the case where motor 11 is of the stepping type, the programmable PROM memory is followed by a digital - analog converter 42 and then a voltage - frequency converter 43. The control circuit of motor 11 can incorporate a plurality of PROM memories, selected as a function of the requirements of the user, who will then choose a servocontrol response curve optimized as a function of the mechanical conditions. In another variant, the correspondence between the servocontrol and the dependent relative distance can be a relationship between the excitation of the motor 11 as a function of the dependent relative distance and the construction parameters. The memory can then be replaced by a processor. The devices 40 to 44 are driven by the clock 48.

According to a special constructional variant, the ultrasonic beam which is unhindered in the air is enclosed in a hollow waveguide. The latter has a shape compatible with that of a path to be traversed by the mechanical component with which it is associated. The waveguide makes it possible to improve the sensitivity of the servocontrol chain in the case where the dependent mechanical component is at a considerable distance from the probe. The reflector associated with the mechanical component is located within the waveguide. It is connected to this component by an arm or an electromechanical means. In the case when the reflector and mechanical component are connected by an arm, the waveguide is slotted to permit the passage of the arm towards the interior of the guide. Such an arrangement enables the mechanical components to be made dependent on non-rectilinear paths. Per se known mode discrimination circuits must then be associated with the detection circuit of each probe.

FIG. 4 shows a constructional variant of a servocontrol according to the invention. In such a device, the reception function of each probe has been readily transferred to the dependent mechanical component. This makes it possible to increase the measuring speed and to consequently improve the precision. On each master - slave channel, there is a transmitter 31 or 32, which transmits an ultrasonic beam to a transducer 29 or 30. Each of the transducers 29 or 30 is connected to a mechanical component, 27 or 28. Each of the mechanical components 27 or 28 is guided on a rail 270 or 280. Each of the detection signals is received by a piezoelectric signal shaping amplifier 33 and 34. Each of their outputs is connected to a control circuit 35 comprising an oscillator 59, whereof one output 351 is validated by a circuit identical to circuit 19. Output 351 can be used as a control for motor means of the slave component 28, a special output 350 of the oscillator can be validated by a monostable flip-flop 54 initialled (20) by the reception of the second of the two detection signals. The pulses supplied by the oscillator are simultaneously transmitted to the ultrasonic wave transmitters 31, 32 during the action time of the monostable flip-flop. When the latter drops again, transmitters 31 and 32 again become silent. They are only reactivated when the second of the two detection signals is received. This device ensures synchronism on servocontrol transmission. It replaces the control devices 45, 47 and 48 of the probes.

There are numerous applications for the present invention. In particular, it is possible for the master mechanical component to be a fixed component. The operation will only fix the image position which must be copied by the slave mechanical component. Probe 3 of FIG. 1 will then be used for calibration for the servocontrol. Probe 4 makes it possible to regulate the position of the slave component 2 to a predetermined distance from the image of the fixed master component 1.

In another application, the ultrasonic beam, having convenient frequencies, is intercepted by the extremities of a patient's body. The measuring system makes it possible to position an X-ray scanner on the organ whose image is to be recorded. Thus, it is known that the ratio of the distance of an organ to the two extremities of the human body is roughly a constant, according to the individual. The knowledge of the position of the head and feet is therefore sufficient to establish the relevant position of any organ from the instantaneous position of the X-ray scanning data acquisition system.

The present invention can be used in all position servocontrol fields where it is a question of copying or recording a given position.

What is claimed is:

1. A servocontrol for controlling ultrasonically the relative position of a master mechanical component and a slave mechanical component movable along guidance means by respective motors comprising:

first and second ultrasonic probe means positioned for directing ultrasonic beams onto said master and slave components respectively and detecting ultrasonic radiation received; and a relative position measuring circuit connected to said probe means for measuring the time interval between receipt of ultrasonic radiation by said master component and ultrasonic radiation by said slave component and producing a displacement signal for controlling the motor displacing said slave component in accordance therewith.

2. A servocontrol as in claim 1 wherein each probe means includes a probe of the transmission-reception type and includes a pulse generator for producing pulses to cause transmission of ultrasonic radiation during said each pulse, a detection circuit for receiving reflected radiation and electronic switch means for periodically switching between said pulse generator and detection circuit.

3. A servocontrol as in claim 2 wherein said relative position measuring circuit includes a flip-flop having a first input connected to said detection circuit of one probe and a second input connected to said detection circuit of the other probe and which changes state at an output at each transition at an input and an AND gate having inputs connected to said output and to an oscillator producing pulses of a predetermined frequency and an output adapted for connection to a control circuit of the slave component motor.

4. A servocontrol as in claim 3 wherein said slave motor is a stepping motor and said control circuit includes a counter receiving the pulses from the output of said AND gate and a programmable memory having address selection inputs connected to said counter and adapted for connection to said slave component motor for supplying a d.c. voltage in programmed steps.

5. A servocontrol as in claim 1 further including an ultrasonic reflector adapted to be mounted on each component, and having a surface substantially normal to the incidence direction of the wave.

6. A servocontrol as in claim 1 wherein said relative position measuring circuit includes a JK flip-flop.

7. A servocontrol as in claim 1 wherein each probe means includes a probe of the transmitter type, an ultrasonic transducer carried by a mechanical component and a shaping amplifier connected to said transducer for producing an output to said relative position measuring circuit.

* * * * *